United States Patent [19]
Gao et al.

[11] Patent Number: 5,760,251
[45] Date of Patent: Jun. 2, 1998

[54] TAXOL PROCESS AND COMPOUNDS

[75] Inventors: Yun Gao, Southborough; Charles M. Zepp, Hardwick, both of Mass.

[73] Assignee: Sepracor, Inc., Marlborough, Mass.

[21] Appl. No.: 589,142

[22] Filed: Jan. 19, 1996

Related U.S. Application Data

[60] Provisional application No. 60/002,140 Aug. 11, 1995.

[51] Int. Cl.$^6$ .................................................. C07D 305/14
[52] U.S. Cl. ................................................ 549/510; 549/511
[58] Field of Search ........................................ 549/510, 511

[56] References Cited

U.S. PATENT DOCUMENTS

| | | | |
|---|---|---|---|
| Re. 34,277 | 6/1993 | Denis et al. | 549/510 |
| 4,857,653 | 8/1989 | Colin et al. | 549/511 |
| 4,924,011 | 5/1990 | Denis et al. | 549/510 |
| 4,924,012 | 5/1990 | Colin et al. | 549/510 |
| 5,015,744 | 5/1991 | Holton | 549/510 |
| 5,229,526 | 7/1993 | Holton | 549/213 |
| 5,274,300 | 12/1993 | Dodds et al. | 435/280 |
| 5,556,877 | 9/1996 | Bouchard et al. | 514/449 |

FOREIGN PATENT DOCUMENTS

| | | | |
|---|---|---|---|
| 0 400 971 | 3/1990 | European Pat. Off. | |
| 0 569 281 | 11/1993 | European Pat. Off. | C07D 305/14 |
| 9301800 | 9/1993 | South Africa | |
| WO 93/21173 | 10/1993 | WIPO | C07D 305/14 |

OTHER PUBLICATIONS

Dondoni et al. "Thiazolyl x–Amino Ketones", Synthesis, 1993, 1162–1176.
Nicolaou et al. "Chemistry and Biology of Taxol" *Angew. Chem. Int. Ed. Engl. 33*, 15–44 (1994).
Kingston "The Chemistry of Taxol" *Pharma. Ther. 52*, 1–34 (1991).
Guénard et al. "Taxol and Taxotere: Discovery, Chemistry, and Structure . . . " *Acc. Chem. Res. 26*, 160–167 (1993).
Georg et al. "Taxane Anticancer Agents–Basic Science and Current Status", Ed, ACS Symposium Series 583 (1995).
Gou et al. "A Practical Chemoenzymatic Synthesis of the Taxol . . . " *J. Org. Chem. 58*, 1287–1289 (1993).
Bonini et al. "Enantio—and Stereo–selective Route to the Taxol Side Chain via Asymmetric . . . " *J. Chem. Soc., Chem. Commun.* 2767–68 (1994).
Bajwa et al. "A Highly Regiosleective Conversion of Epoxides to Holohydrins . . . " *Tetrahedron Letters 32*, 3021–3024 (1991).
Wang et al. "Large–Scale and Highly Enantioselective Synthesis of the Taxol C–13 Side . . . " *J. Org. Chem. 59*, 5104–5105 (1994).

*Primary Examiner*—Ba K. Trinh
*Attorney, Agent, or Firm*—Heslin & Rothenberg, P.C.

[57] ABSTRACT

A process for the preparation of taxol and derivatives of taxol

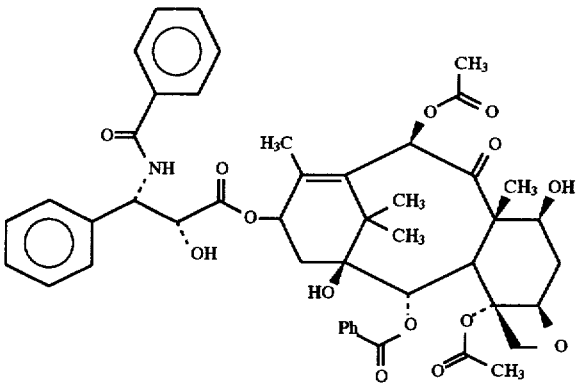

is disclosed. The process involves reacting a β-alkoxycarbonylamino-phenylpropionic acid with a 13-hydroxy taxane to produce an ester of the taxane at C-13; and then deprotecting the β-alkoxycarbonylamino-phenylpropionic ester to produce a β-amido-α-hydroxybenzenepropanoic ester of the taxane. Intermediates useful in the process are also disclosed.

7 Claims, No Drawings

TAXOL PROCESS AND COMPOUNDS

CROSS REFERENCE TO RELATED APPLICATIONS

This application claims the benefit of U.S. Provisional application Ser. No. 60/002,140, filed Aug. 11, 1995.

FIELD OF THE INVENTION

The invention relates to a process for the preparation of taxol I and derivatives of taxol

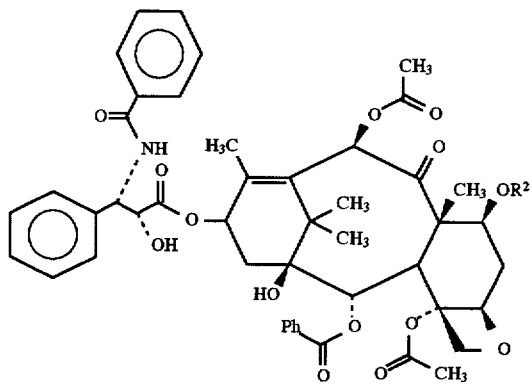

I and to intermediates useful in the process.

BACKGROUND OF THE INVENTION

Taxol (I) is currently in clinical trials and has demonstrated efficacy with manageable side effects in 30 to 35% of cases of ovarian cancer and 56% of cases of metastatic breast cancer, but large scale clinical trials have been hampered by the small available supplies of the drug.

Taxol, whose generic name as a drug is paclitaxel, is currently produced by extraction from the bark of the Pacific yew, *Taxus brevifolia*. The Pacific yew is a slow growing conifer found in the understory of old growth stands in the Pacific Northwest. Ten thousand kilograms of bark are required to produce one kilogram of taxol, which is enough to treat only 500 patients. For this reason the chemical synthesis of taxol has aroused great interest. However, the sterically crowded, chemically sensitive and chirally complex taxane ring structure

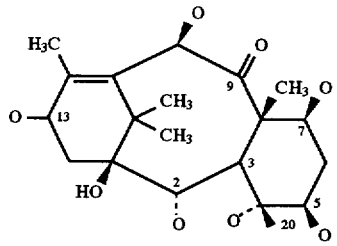

II has essentially forestalled any practical synthesis de novo. As a result, current chemical efforts are focused on semi-synthesis from more readily available congeners. The chemistry of taxol and related diterpenoids has been described in two excellent recent review articles [Kingston, *Pharm. Ther.* 52, 1–34 (1991) and Nicolaou et al. *Angew. Chem. Int. Ed.* 33, 15–44 (1994)], the entire disclosures of which are incorporated herein by reference.

Although no good source of taxol has been found, a related compound baccatin III,

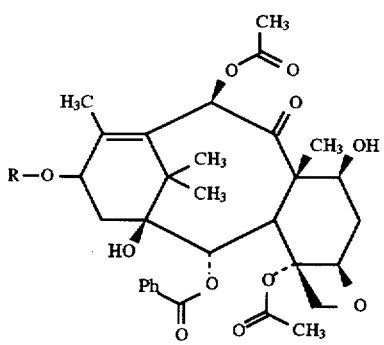

III wherein R is hydrogen, is much more readily available from the needles of the European yew, *Taxus baccata*. This has led to a very active exploration of semi-synthetic routes from baccatin to taxol. The most practical present routes of semi-synthesis involve the attachment of the side chain of taxol

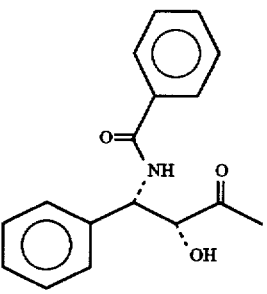

IV onto a suitably protected baccatin, followed by deprotection.

Several of the known routes for the semi-synthesis of taxol proceed through a substantially optically pure azido ester of the formula V:

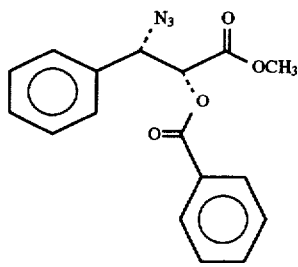

V

The azide is reduced, resulting in a trans-acylation from oxygen to nitrogen;

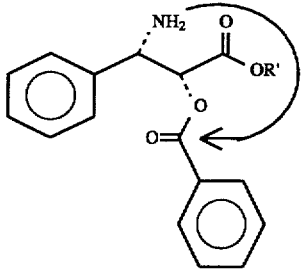

VI the hydroxyl of the resulting β-amido ester VII

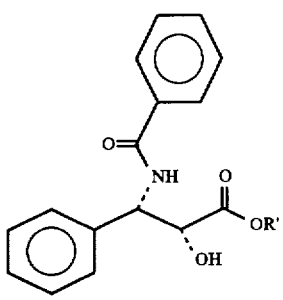

VII is protected; and the ester is saponified to produce the protected carboxylic acid VIII:

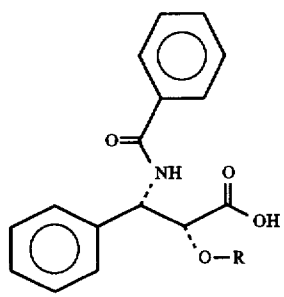

VIII

This protected acid is then coupled with the suitably protected taxane ring system. Consistent with common usage, the term "taxane" is understood to encompass diterpenoids having a 6,10-methanobenzocyclodecane ring structure oxygenated at least at the 3,5,8,11 and 12 positions and carbon-substituted at 4,6,9,12a,13 and 13. In the case of taxanes of present therapeutic interest (having the baccatin and taxol ring structures), the oxygen at position 8 of the methanobenzocyclodecane is an alcohol (which will be esterified) and the carbon at 4 and the oxygen at 3 are cyclized to form an oxetane ring. Structure II above reflects the pattern of substitution of the taxanes of interest and shows the numbering system commonly used for taxol, which is different from the numbering system of the parent methanobenzocyclodecane.

SUMMARY OF THE INVENTION

The process of the invention shown in Scheme A provides an improved synthesis of taxol and related structures by the coupling of an optically pure β-protected amino carboxylic acid (IX) with the suitably protected taxane ring structure X in which $R^2$ is a protecting group for an alcohol (see below):

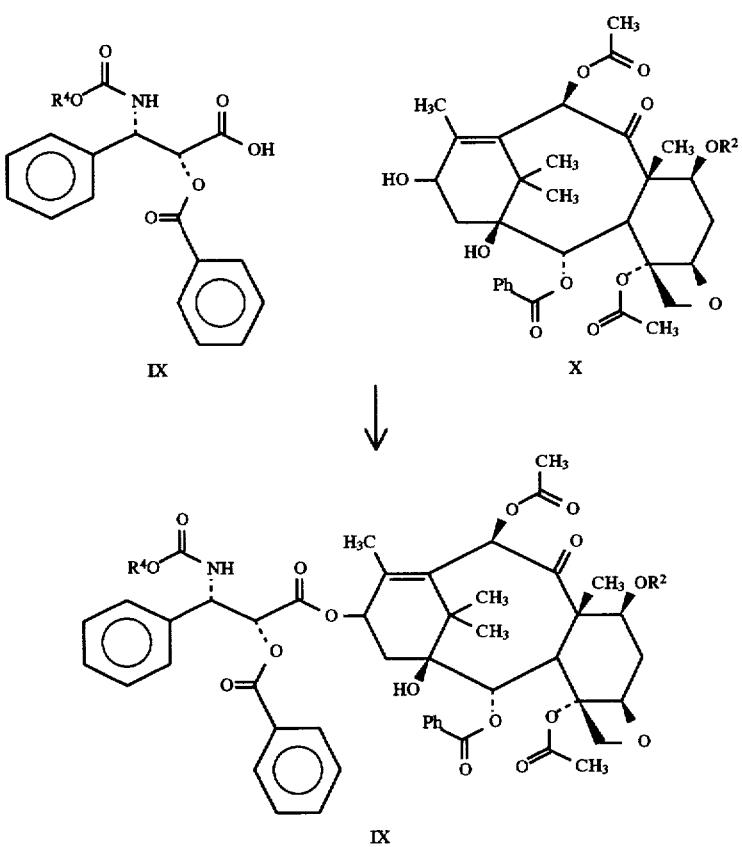

Scheme A

The amino protecting group is then removed to liberate the free amine, which undergoes internal transacylation to produce the desired α-hydroxyl β-amido sidechain in the taxol.

In one aspect, the invention relates to a process for the preparation of taxol, and derivatives thereof, comprising: (a) reacting a β-alkoxycarbonylamino-phenylpropionic acid of formula (XII) wherein $R^1$ is $C_1$ to $C_{10}$ alkyl, phenyl or substituted phenyl; $R^3$ is hydrogen, loweralkyl, loweralkoxyl, di-loweralkylamino or halo; and $R^4$ is benzyl (Cbz), t-butyl (tBoc), allyl (Aloc), trichloroethyl (Troc), or 9-fluorenylmethyl (Fmoc), with a 13-hydroxy taxane to produce an amidophenylpropionic ester at C-13 of the taxane;

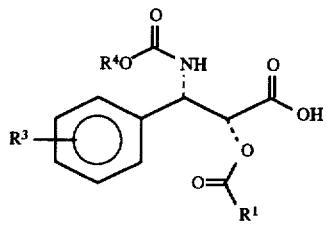

XII and (b) removing the β-amino protecting group by treatment with an acid or by reduction followed by internal acyl transfer to produce a β-amido-α-hydroxyphenylpropionic ester of the taxane. Preferred $R^1$ substituents are phenyl, substituted phenyl (particularly 4-chlorophenyl) or t-butoxyl; the preferred $R^3$ is hydrogen. The term "alkyl" as used herein refers to saturated hydrocarbons, including straight and branched chains as well as cyclic structures such as cyclohexyl. Lower alkyl refers to alkyl of six or fewer carbons. The definitions of substituents are presented herein in their first occurrence and retain that definition throughout the text.

In a more specific embodiment, the process of the invention relates to a process as above comprising (a) reacting a β-alkoxycarbonylamino-phenylpropionic acid of formula (IX), wherein $R^4$ is t-butyl, benzyl or 9-fluorenylmethyl,

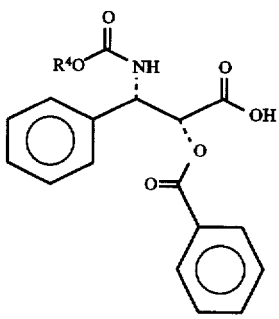

IX with a taxane of formula (X)

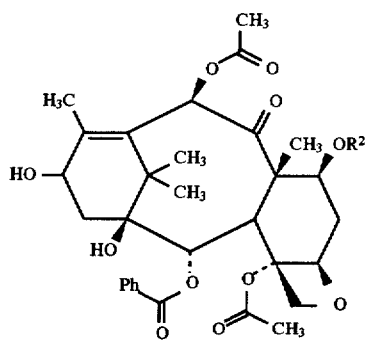

X to produce an alkoxycarbonylaminophenylpropionic ester at C-13 of formula (XI)

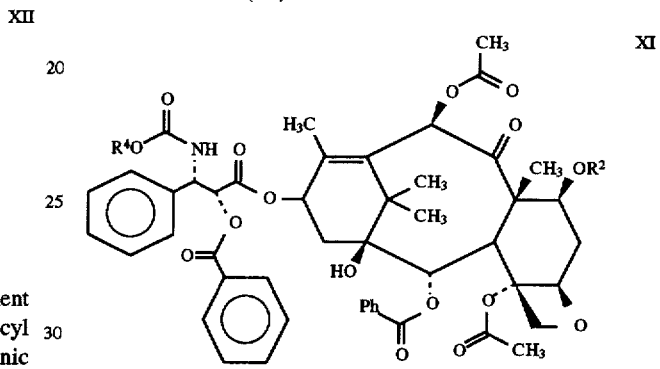

XI and (b) removing the alkoxycarbonyl protecting group of the phenylpropionic ester of taxane to produce a β-amido-α-hydroxyphenylpropionic ester of taxane of formula XIII:

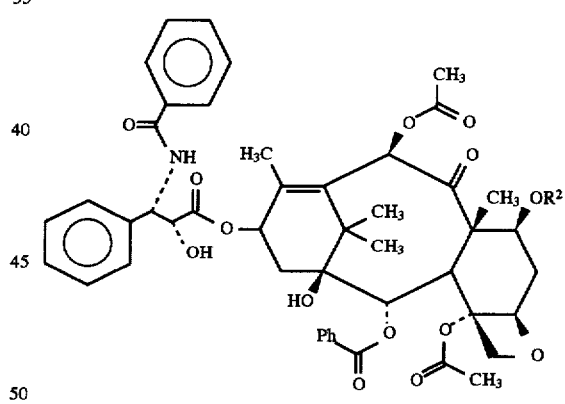

XIII wherein $R^2$ is a protecting group for an alcohol. The term "protecting group for an alcohol" refers to a residue that is stable under the conditions of the condensation of the benzenepropanoic acid with the 13-hydroxy taxane, but that can be cleaved to an alcohol under conditions that do not otherwise affect the β-amido-α-hydroxybenzenepropanoic ester of the taxane. Suitable protecting groups include 1,1,1-trichloroethoxycarbonyl (Troc), removable by zinc in acetic acid and aryldialkylsilanes or trialklsilanes, removable by mild acid such as 0.5% HCl in methanol. A preferred protecting group for the C-7 hydroxyl is trihexylsilyl.

The process of the invention may further comprise the additional step of cleaving the protecting group $R^2$ to produce taxol, and the step of deprotecting the β-aminobenzenepropanoic ester may also cleave the protecting group $R^2$, whereby a 2′,7-dihydroxy-3′-amidoester is produced in a single reaction.

In a further aspect, the invention relates to compounds of formula XIV:

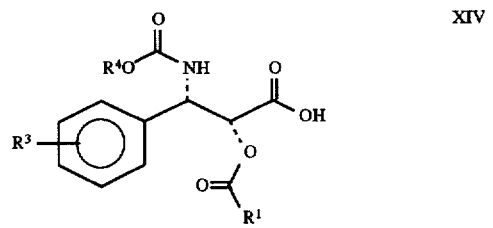

wherein $R^1$ is $C_1$ to $C_{10}$ alkyl, $C_1$ to $C_{10}$ alkoxyl, phenyl or substituted phenyl; $R^3$ is hydrogen, loweralkyl, loweralkoxyl, di-loweralkylamino or halo and $R^4$ is allyl, benzyl, t-butyl, or 9-fluorenylmethyl. The compounds are novel and are useful for preparing taxol according to the method of the invention. Preferred compounds are those in which $R^1$ is phenyl, t-butoxyl or 4-chlorophenyl and $R^3$ is hydrogen.

In a further embodiment, the invention relates to compounds of formula XV

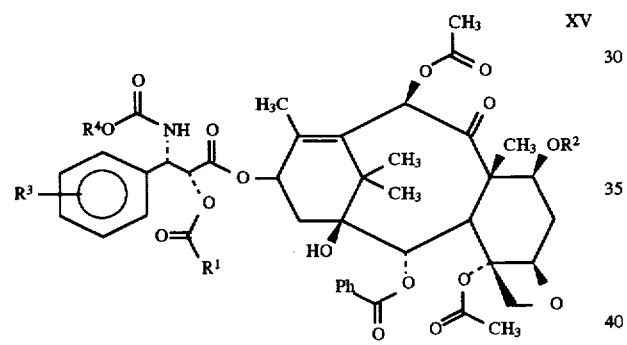

wherein $R^2$ is trialkylsilyl (e.g. t-butyldimethylsilyl, trihexylsilyl, triethylsilyl or trimethylsilyl), or aryldialkylsi- lyl (e.g. phenyldimethylsilyl) and the other substituents are as defined before. The compounds are useful as intermediates in the process of the invention.

DETAILED DESCRIPTION OF THE INVENTION

The central process of the invention involves the reaction of a suitably protected 13-hydroxy-taxane X with a β-alkoxycarbonylamino-phenylpropionic acid XIV to form the ester XV. In a second step the amine is deprotected by procedures known in the art, such as hydrogenation in the presence of a catalyst (for $R^4$=benzyl) or treatment with mild acid (for $R^4$=t-butyl), whereupon the acyl group is transferred from the α-oxygen to the newly created β-amino function. The C-7 hydroxyl of baccatin is the most reactive hydroxyl and must commonly be protected during the reaction to form the ester. It will then be deprotected in a final step to produce taxol or a taxol analog. The reaction is shown below in Scheme B, which is a generic version of Scheme A:

SCHEME B

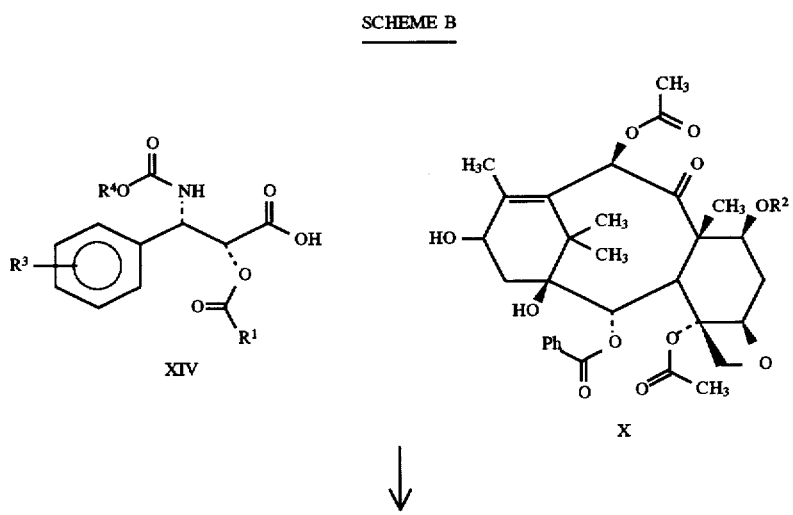

-continued
SCHEME B
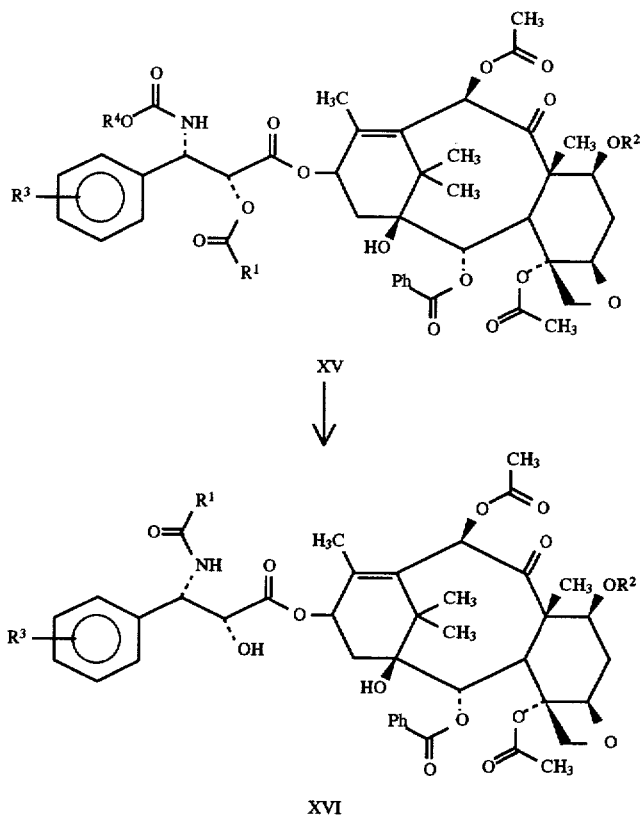
The process of the invention is distinguished from processes of the art (shown in Scheme C) in which an α-hydroxyl-protected β-amidobenzenepropanoic acid XVII
SCHEME C
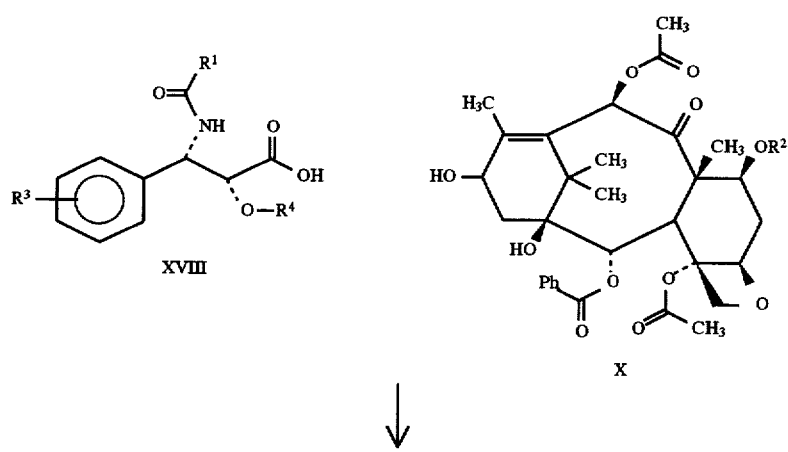

-continued
SCHEME C

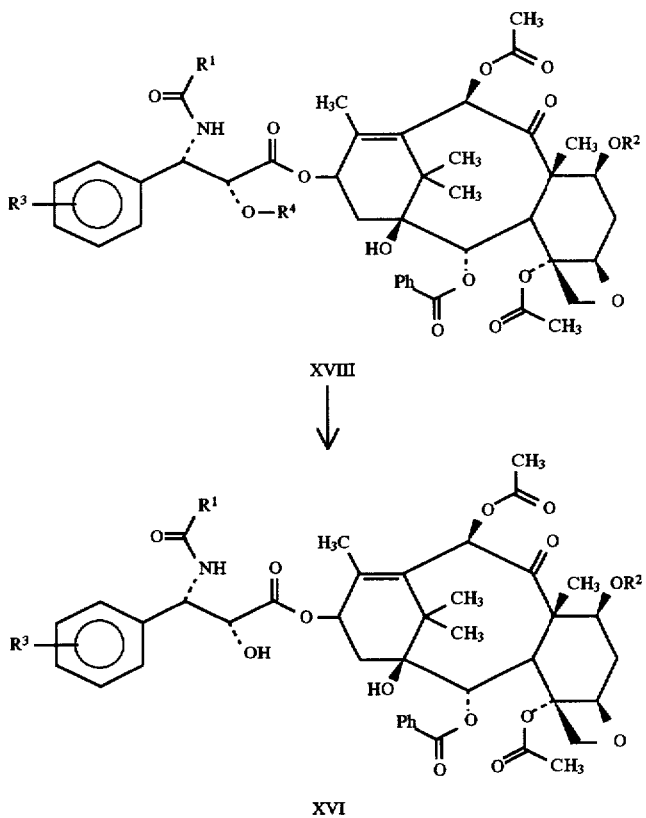

is reacted with the suitably protected taxane X and the protecting group R⁴ is subsequently removed from the α-hydroxyl.

The optically pure β-alkoxycarbonylaminophenylpropionic acid XIV

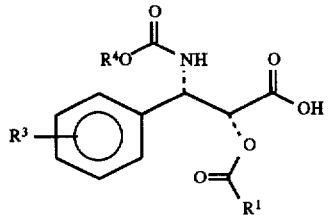

may be prepared by a number of possible routes. In one synthetic route (Scheme D),

SCHEME D

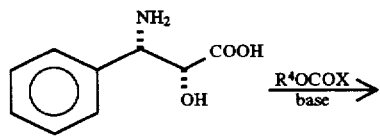

-continued
SCHEME D

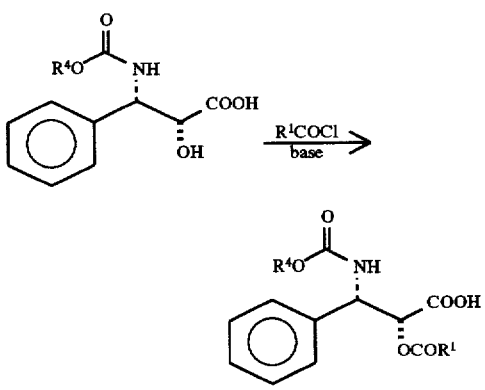

readily available optically pure (2R, 3S)-phenylisoserine is treated with an alkyl chloroformate or equivalent such as di-t-butyl dicarbonate [(Boc)₂O] under Schotten-Baumann conditions (aq. NaOH or K₂CO₃) to give the β-alkoxycarbonylamino-α-hydroxyl acid. The α-hydroxyl of the acid is then reacted with an acid chloride such as benzoyl chloride in the presence of a base such as aqueous NaOH to give the desired β-alkoxycarbonylaminophenylpropionic acid after neutralization and purification.

Alternatively, as shown in Scheme E, the β-alkoxycarbonyl-aminophenylpropionic acid can be synthesized from optically pure ethyl (2R,3S)-phenylglycidate, which is obtained by enzymatic resolution of the racemic glycidate according to the method of U.S. Pat. No. 5,274, 300, the relevant disclosure of which is incorporated herein by reference, or from ethyl (2R,3S)-2,3-dihydroxy-3-phenylpropionate according to the procedure of Kolb et al [*Tetrahedron* 48, 10515 (1992)], which is incorporated herein by reference. The ethyl (2R,3S)-phenylglycidate is then converted to the trimethylsilylethyl ester by treatment with 2-trimethylsilylethanol in the presence of a base such as 1,8-diazabicyclo[5.4.0]undec-7-ene (DBU). The resulting epoxide is opened with a source of Br⁻, such as lithium bromide in acetic acid/THF or diethylamine hydrobromide, in the presence of an aluminum compound, such as diethylaluminum chloride, to produce (2R,3R)-3-bromo-2-hydroxy-3-phenylpropionate XXIII, which is then treated with sodium azide in DMF to produce the β-azidopropionate. The 3-azido-2-hydroxy ester is then reduced to the β-amino ester which is then treated with an alkyl chloroformate (R⁴OCOCl) followed by an acid chloride (R¹COCl), such as benzoyl chloride, to produce the appropriate 3-alkoxycarbonylamino-2-acyloxyphenylpropionate ester.

(1993)], Bajwa et al. [*Tetrahedron Letters* 32, 3021–3024 (1991)] and Bonini et al. [*J. Chem. Soc. Chem. Commun.* (1994) 2767–2768], the disclosures of which are incorporated herein by reference.

The condensation of the β-alkoxycarbonylaminophenylpropionic acid with a suitably protected baccatin can be carried out using standard ester formation methods. Preferably, the condensation of the baccatin with the acid sidechain is performed using at least one equivalent of the acid in the presence of at least one equivalent of activating reagent such as dialkylcarbodiimide, di-2-pyridylcarbonate and PhOPOCl₂ or Me₂NPOCl₂ and a base such as 4-dimethylaminopyridine (DMAP) or 4-pyrrolidinopyridine (4-PP) in an inert solvent. Most preferably, the condensation is performed using 1.2–1.5 equivalents of the acid XIV in the presence of 1.2–1.5 equivalents of DCC or DIC and 0.2–0.5 equivalents of DMAP or 4-PP in toluene at 40°–50° C. for 4–10 hours.

When R⁴ of the alkoxycarbonylaminophenylpropionic acid is t-butyl and R² of the 7-hydroxyl protecting group is

SCHEME E

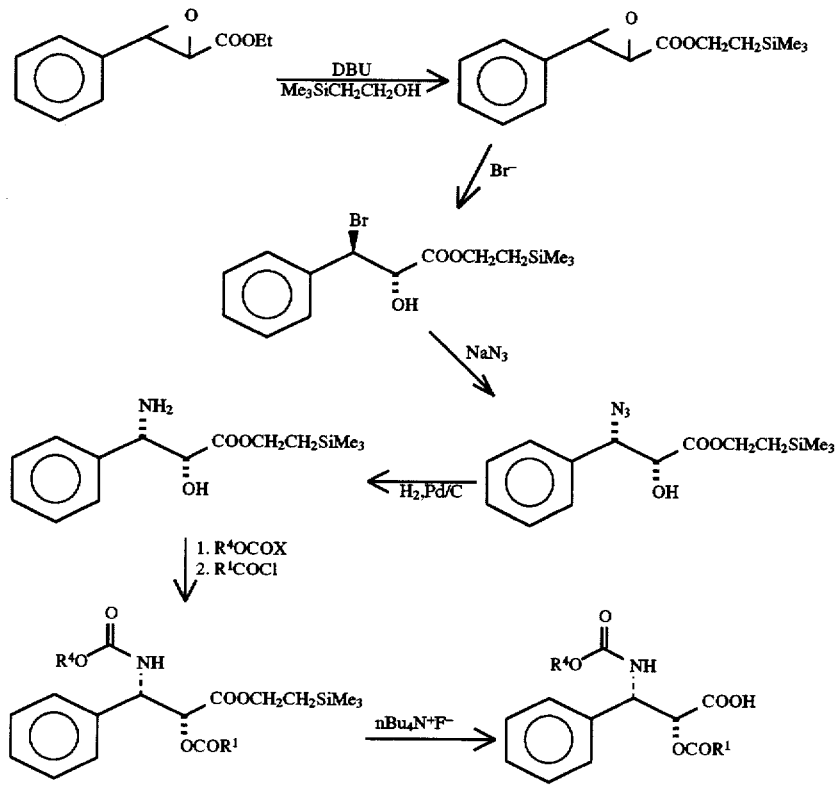

Alternatively, the 3-azido-2-hydroxy ester is treated with an acid chloride (R¹COCl), such as benzoyl chloride, to give the 3-azido-2-acyloxy ester which is then hydrogenated in the presence of di-alkyl-dicarbonate, such as Boc₂O, under 1 atm of hydrogen over a catalyst, such as Pd/C, to give the 3-alkoxycarbonylamino-2-acyloxyphenylpropionic ester. The trimethylsilylethyl ester is then treated with tetrabutylammonium fluoride in THF to give the 3-alkoxycarbonylamino-2-acyloxyphenylpropionic acid after acidification.

Alternative syntheses of various of the intermediates in the synthesis of the β-azido benzenepropanoic acid have been published by Gou et al. [*J. Org. Chem.* 58, 1287–1289 a silyl group, the conversion of the condensation product to taxol and analogs is most conveniently accomplished in acidic medium such as trifluroacetic acid (TFA) in methylene dichloride or THF or in neat formic acid. When R⁴ is benzyl, allyl, or 9-fluorenylmethyl and R² is silyl, the conversion is accomplished by removal of the silyl group with an acid, as above, or with HF/pyridine or with tetrabutylammonium fluoride in THF followed by catalytic hydrogenation using Pd/C or Pd(PPh₃)₄ and hydrogen or a hydrogen donor such as ammonium formate.

When R⁴ is trichloroethyl and R² is trichloroethoxycarbonyl, the conversion is accomplished by reduction with zinc in HOAc. Under these conditions, the taxol is recovered by neutralization with an aqueous solution of sodium bicarbonate in an inert solvent such as ethyl acetate, toluene or methylene dichloride, followed by purification by crystallization or chromatography on silica gel.

Several possible alcohol protecting groups $R^2$ for the C-7 hydroxyl were compared as to ease of protection and deprotection, stability of the product towards further reaction conditions, selectivity of the reaction for the protection of the desired functional group over other hydroxyl groups in the molecule, ease of purification and cost of the materials. As a part of the exploration of $R^2$ groups, the acetylation of the C-10 hydroxyl group was also studied, and the results of this study are presented in the experimental section below.

10-Deacetyl baccatin-III (10-DAB) was treated with a variety of reagents under a number of reaction conditions. It appears that silyl protecting groups were more well behaved than other common protecting groups. Treatment of 10-DAB with triethylsilyl chloride and imidazole in DMF resulted in the smooth preparation of the triethyl silyl ether in 70% yield. Under similar conditions, treatment with t-butylmethoxphenylsilyl bromide resulted in the silylated taxoid in a yield of 89%. The phenyldimethyl silyl derivative was prepared in an acceptable yield of 74%.

A preferred protecting group is tri-n-hexylsilyl. When treated with tri-n-hexylsilyl chloride, 10-DAB underwent smooth silylation to produce the C-7 silylated material in 80% yield. Very importantly, the pure tri-n-hexylsilyl ether product is obtained by recrystallization. No chromatography is necessary.

Acetylation at C-10 of the C-7 silylated substrates was accomplished by treatment with acetyl chloride in pyridine at 0° C. Acetylation of both the triethylsilyl and tri-n-hexylsilyl ethers proceeded to give the desired acylation at the C-10 hydroxyl group. Although in both cases some desilylation occurred, it is postulated that this side reaction, which is probably induced by hydrochloric acid generated during the reaction, may be suppressed by modification of the existing conditions or by acylation of the discrete alkoxide. The more labile phenyldimethylsilyl group is cleaved to a greater extent than the trialkylsilyl ethers under the same reaction conditions. The unoptimized yield for the acylation of the tri-n-hexylsilyl derivative is 70%.

The removal of the C-7 silyl protecting group may be accomplished by HF in pyridine, resulting in clean conversion to the free alcohol. Cleavage of the tri-n-hexylsilyl ether was slower than the triethylsilyl ether; the yield for the tri-n-hexylsilyl ether deprotection was 68%. In the case of the 7-TES derivative, HF in acetonitrile proved too harsh and resulted in the production of a complex mixture of products.

The presently preferred candidate for C-7 hydroxyl protection is the tri-n-hexylsilyl ether. Tri-n-hexylsilyl chloride has similar reactivity to triethylsilyl chloride and is cheaper than triethylsilyl chloride; the intermediate ether can be purified by recrystallization; and the protecting group can be cleanly cleaved.

Although the synthesis has been illustrated with compounds in which $R^1$ is phenyl and $R^3$ is hydrogen, the person of skill will readily appreciate that analogous reactions could be carried out employing starting materials and intermediates in which $R^1$ is other than phenyl and $R^3$ is other than hydrogen.

EXAMPLES

Example-1

(2R,3S)-phenylisoserine hydrochloride (6.0 g, 27.6 mmol) was dissolved in H₂O/tBuOH (50 mL each) at room temperature. A solution of NaOH (50% aq., 4.6 g, 58 mmol) was added followed by di-t-butyl dicarbonate (7.23 g, 33.1 mmol). The resulting mixture was stirred at room temperature overnight and concentrated to ca. 30 mL. The residue was diluted with EtOAc (150 mL) and acidified with 1N $H_2SO_4$ to pH 3–4. The aq. phase was separated and extracted with 50 mL of ethyl acetate (EtOAc). The combined organic phase was washed with sat'd NaCl and dried over $Na_2SO_4$. After filtration and concentration, the resulting yellow solid was recrystallized from EtOAc/heptane to give (2R,3S)-3-t-butyloxycarbonylamino-2-hydroxyphenylpropionic acid as a white solid (5.9 g, 75.6% yield).

Example-2

(2R,3S)-3-t-butyloxycarbonylamino-2-hydroxyphenylpropionic acid (1.41 g, 5 mmol) was dissolved in H₂O/acetone (10 mL each) containing 0.4 g of 50% aq. NaOH (5 mmol). The solution was cooled with ice water. Benzoyl chloride (1.2 mL, 10 mmol) and 1N NaOH solution were added alternatively in small portions while maintaining the pH at ca. 10–11. After addition, the mixture was stirred at room temperature for 2 h at pH 9–11. The mixture was then diluted with EtOAc (100 mL) and acidified with 1N $H_2SO_4$ to pH 2–3. The aq. phase was separated and extracted with 30 mL of EtOAc. The combined organic phase was washed with sat'd NaCl and dried over $Na_2SO_4$. The crude product was then purified on silica gel eluting with EtOAc/hexane and EtOAc to give (2R,3S)-3-t-butyloxycarbonylamino-2-benzoyloxyphenylpropionic acid as a white solid (0.96 g, 50 % yield).

Example-3

Ethyl (2R,3S)-phenylglycidate (36 g, 0.19 mol) was treated with 2-trimethylsilylethanol (67 g, 0.57 mol) in toluene (100 mL) in the presence of catalytic amount of DBU at 60°–80° C. for 2–3 days. The reaction was then concentrated under vacuum to give the crude trimethylsilyl ethyl ester (ca. 50 g). The crude ester was dissolved in THF (150 mL) and cooled with icewater. Acetic acid (44 mL, 0.8 mol) was added followed by LiBr (49 g, 0.56 mol) in three portions. The mixture was stirred from 5° C. to room temperature for 26 h and was concentrated to dryness to remove THF. The residue was diluted with 100 mL of H₂O and extracted with 2×300 mL of methyl t-butyl ether (MTBE). The MTBE extracts were then washed with water (50 mL) and sat'd NaCl and concentrated to give a crude oil which was purified on silica gel eluting with hexane and 10% EtOAc in hexane to give a white solid (12.4 g, 19% yield) as the (2R,3R)-3-bromo-2-hydroxyphenylpropionic acid 2-trimethylsilylethyl ester.

Example-4

The ester from Example-3 (12.3 g, 35.6 mmol) was treated with $NaN_3$ (7.0 g, 0.11 mol) in 40 mL of DMF at 60°–70° C. for 18 h. The mixture was cooled and diluted with 50 mL of water and extracted with 300 mL of MTBE. The MTBE solution was washed with water (40 mL) and sat'd NaCl (30 mL) and concentrated to give a crude oil which was purified on silica gel eluting with hexane and 10% EtOAc/hexane to give (2R,3S)-3-azido-2-hydroxyphenylpropionic acid 2-trimethylsilylethyl ester (11.0 g, 100% yield).

Example-5

The azido ester from Example-4 (11.0 g, 35.6 mmol) was hydrogenated on a Parr-shaker at 50 psi in ethanol (EtOH)

in the presence of catalytic amount of Pd/C (2.0 g). After removal of the catalyst and concentration, the resulting 3-amino-2-hydroxyphenylpropionic ester was dissolved in tetrahydrofuran (THF) (50 mL) and treated with di-t-butyl dicarbonate (9.3 g, 42.7 mmol) and $Et_3N$ (7.2 g, 71.2 mmol) at room temperature overnight. The mixture was concentrated and diluted with MTBE (250 mL) and washed with water and brine. After drying and concentration, the residue was purified on silica gel eluting with hexane and 10% EtoAc/hexane to give (2R,3S)-3-t-butyloxycarbonylamino-2-hydroxyphenylpropionic acid 2-trimethylsilylethyl ester (12.0 g, 90% yield).

Example-6

The ester (12 g, 31.5 mmol) from example-5 was dissolved in THF (50 mL) and cooled with icewater. Et3N (6.4 g, 63 mmol) was added, followed by benzoyl chloride (5.3 g, 38 mmol) dropwise with cooling. The resulting mixture was stirred at room temperature overnight and diluted with EtOAc (250 mL) and quenched with 50 mL of water. The aq. phase was separated and the organic phase was washed with dilute $H_2SO_4$, water and then sat'd aq. NaHCO3. After drying, the crude product was purified on silica gel eluting with hexane and 10% EtOAc/hexane to give (2R,3S)-3-t-butyloxycarbonylamino-2-benzoyloxyphenylpropionic acid 2-trimethylsilylethyl ester (13.8 g, 90% yield).

Example-7

The ester (13.8 g, 28.4 mmol) from Example-6 was dissolved in THF (50 mL) and cooled with icewater. Tetrabutylammonium fluoride in THF (1.0M in THF, 57 mL) was added dropwise. The resulting solution was stirred at room temperature for 7 h and concentrated to dryness. The residue was dissolved in 300 mL of EtOAc and acidified with 1N $H_2SO_4$ to pH 3–4. The EtOAc solution was then washed with water (20 mL) and sat'd NaCl (20 mL) and concentrated to dryness. The crude product was purified on silica gel eluting with EtOAc to give (2R,3S)-3-t-butyloxycarbonylamino-2-benzoyloxyphenylpropionic acid as a white solid (8.7 g, 80% yield).

Example-8

The 3-azido-2-hydroxy ester from Example-4 (11.0 g, 35.6 mmol) was dissolved 100 mL of EtOAc and 50 mL of THF. Triethylamine (10 mL, 71.2 mmol) was added and the solution was cooled with icewater. Benzoyl chloride (4.2 mL, 36 mmol) was added and the mixture was stirred at room temperature for 20 h. The mixture was quenched with 50 mL of water and diluted with 150 mL of EtOAc. The organic phase was separated and washed with dilute $H_2SO_4$, water and sat'd NaCl and concentrated. The residue was then purified on silica gel eluting with hexane and 7% EtOA/hexane to give 3-azido-2-benzoyloxyphenylpropionic acid 2-trimethylsilylethyl ester as a pale yellow oil (10.6 g, 72% yield).

Example-9

The 3-azido-2-benzoyloxy ester from Example-8 (2.06 g, 5 mmol) was dissolved in EtOAc (20 mL) and di-t-butyldicarbonate (2.2 g, 10 mmol) and 0.2 g of 10% Pd/C were added. The mixture was hydrogenated at 1 atm with stirring at room temperature for 4 days and then filtered. The filtrate was concentrated to give a residue which was purified on silica gel eluting with hexane and 10% EtOAc/hexane to give 3-t-butyloxycarbonylamino-2-benzoyloxyphenylpropionic acid 2-trimethylsilylethyl ester as a glassy solid (2.0 g, 84% yield).

Example-10

The ester from Example-9 (2.0 g, 4.22 mmol) was dissolved in 20 mL of THF and $nBu_4NF$ in THF (1.0M, 8.5 mL, 8.5 mmol) was added. The solution was stirred at room temperature for 3 h and concentrated to dryness. The residue was dissolved in EtOAc (150 mL) and acidified with dilute $H_2SO_4$ to pH 3–4. The organic phase was then washed with sat'd NaCl and concentrated. The residue was purified on silica gel eluting with EtOAc to give a white solid as (2R,3S)-3-t-butyloxycarbonylamino-2-benzoyloxyphenylpropionic acid (1.28g, 78.5% yield).

Example-11

10-Deacetylbaccatin III (1 g, 1.8 mmol) and imidazole, (980 mg, 14.4 mmol) were dissolved in 60 mL dry DMF under an atmosphere of argon in a 200 mL roundbottom flask equipped with a stirring bar. Tri-n-hexylsilyl chloride (4 mL, 10.8 mmol) was added and the mixture was stirred for 6 h at room temperature. Ethyl acetate and water were added and the phases allowed to separate. The organic layer was separated and the aqueous phase was washed with brine and dried over anhydrous $MgSO_4$. After filtration and evaporation of the solvent under reduced pressure, the crude product was recrystallized from methylene chloride and hexanes to yield 1.11 g of the pure product (74% yield); mp. 203° C.

Example-12

7-Tri-n-hexylsilyl-10-deacetylbaccatin III (250 mg, 0.3 mmol) from example 11 was dissolved in 7.7 mL of anhydrous pyridine under an argon atmosphere in a 25 mL roundbottom flask equipped with a stirring bar. The solution was cooled to 0° C. and acetyl chloride (100 L, 1.5 mmol) was added dropwise. The mixture was stirred for 20 h at 0° C. A further 100 µL of acetyl chloride was added and the mixture stirred for another 20 h at 0° C. Ethyl acetate was added, followed by water at 0° C. The organic phase was removed and the aqueous phase was extracted twice with ethyl acetate. The organic layers were combined and washed with saturated $CuSO_4$ solution, (until the pyridine had been completely removed), water and brine and finally dried over anhydrous $MgSO_4$. After filtration, and removal of the solvent under reduced pressure, the resulting residue was purified by flash chromatography on silica gel (elution with 30–50% ethyl acetate/hexanes) to yield 171 mg of pure product (66% yield).

Example-13

7-Tri-n-hexylsilylbaccatin III (250 mg, 0.3 mmol) from example 12 was dissolved in 15 mL of anhydrous THF under an atmosphere of argon in a 50 mL round-bottom flask equipped with a stirring bar. HF-pyridine (3 mL) was then added dropwise. The reaction mixture was stirred for 2 h at 25° C. Ethyl acetate and water were added. After separation of the phases, the aqueous phase was extracted twice with ethyl acetate. The combined organic extracts were washed with saturated copper sulphate, water and brine, and dried over anhydrous magnesium sulphate. After filtration and removal of the solvent under reduced pressure, the residue was purified by flash chromatography on silica gel (elution with 70–100% ethyl acetate/hexanes) to yield 111 mg of pure baccatin III (68% yield).

Example-14

A mixture of (2R,3S)-3-t-butyloxycarbonylamino-2-benzoyloxyphenylpropionic acid (78 mg, 0.2 mmol) (Example 10), dicyclohexylcarbodiimide (DCC) (41 mg, 0.2 mmol), 4-pyrrolidinopyridine (15 mg, 0.1 mmol) and 7-triethylsilyl baccatin (TES-baccatin) (70 mg, 0.1 mmol) in 0.3 mL of dry toluene was heated at 50° C. for 6 h. The mixture was then concentrated and purified on silica gel eluting with hexane and 30% EtOAc/hexane to give the (2R,3S)-3-t-butyloxycarbonylamino-2-benzoyloxyphenylpropionic acid ester of 7-TES-baccatin at the C-13 hydroxyl group as a white solid (100 mg, 93% yield).

Example-15

A mixture of (2R,3S)-3-t-butyloxycarbonylamino-2-benzoyloxyphenylpropionic acid (78 mg, 0.2 mmol), diisopropylcarbodiimide (DIC) (38 mg, 0.3 mmol), 4-pyrrolidinopyridine (15 mg, 0.1 mmol) and 7-TES-baccatin (94 mg, 0.134 mmol) in 0.5 mL of dry toluene was heated at 50° C. for 6.5 h. The solution was then cooled and diluted with EtOAc/toluene and washed with water, dilute $H_2SO_4$ and sat'd NaCl. The solution was concentrated to dryness to give crude (2R,3S)-3-t-butyloxycarbonylamino-2-benzoyloxyphenylpropionic acid ester of 7-TES-baccatin (200 mg).

Example-16

As an alternative to example 5, the (2R,3S)-3-azido-2-hydroxyphenylpropionic acid, 2-trimethylsilylethyl ester from Example-4 (6.2 g, 20.2 mmol) was treated with ammonium formate (5 g, 80 mmol) in the presence of 10% Pd/C (0.6 g) in 50 mL of methanol for 3–5 hours. The reaction mixture was filtered to remove the catalyst and the filtrate was concentrated to dryness. The residue was diluted with 150 mL of ethyl acetate and washed with water and sodium bicarbonate solution. After concentration, the crude product was purified on silica gel eluting with ethyl acetate and 10% methanol in ethyl acetate to give pure (2R,3S)-3-amino-2-hydroxyphenylpropionic acid, 2-trimethylsilylethyl ester as a yellow sticky oil (4.0 g, 70% yield).

Example-17

The amino alcohol from Example-16 (2.2 g, 7.8 mmol) and Et3N (2.2 mL, 15.6 mmol) were dissolved in 10 mL of THF and cooled with ice water. Benzyl chloroformate (Cbz-Cl) (1.4 mL, 9.36 mmol) was added dropwise to the solution. The resulting white slurry was stirred at room temperature for 2 h. The reaction mixture was diluted with 150 mL of ethyl acetate and washed with water, dilute sulfuric acid and sat'd NaCl solution. The crude product was then purified on silica gel eluting with hexane and 10% ethyl acetate in hexane to give the (2R,3S)-3-benzyloxycarbonylamino-2-hydroxyphenylpropionic acid, 2-trimethylsilylethyl ester (1.33 g, 41% yield).

Example-18

The (2R,3S)-3-benzyloxycarbonylamino-2-hydroxyphenylpropionic acid, 2-trimethylsilylethyl ester (1.33 g, 3.2 mmol) from Example-17 and triethylamine (0.9 mL, 6.4 mmol) were dissolved in 10 mL of THF and cooled with ice water. Benzoyl chloride (0.41 mL, 3.53 mmol) was added dropwise. The mixture was stirred at room temperature overnight and worked up and purified as in Example-14 to give the (2R,3S)-3-benzyloxycarbonylamino-2-benzoyloxyphenylpropionic acid, 2-trimethylsilylethyl ester (1.1 g).

Example-19

The (2R,3S)-3-benzyloxycarbonylamino-2-benzoyloxyphenylpropionic acid, 2-trimethylsilylethyl ester (1.1 g) from Example-18 was dissolved in 5 mL of THF and cooled with ice water. A solution of $Bu_4NF$ in THF (1.0M, 6 mL) was added. The solution was stirred at room temperature for 2–4 h and concentrated to dryness. The residue was dissolved in 100 mL of ethyl acetate and acetified with dilute sulfuric acid and washed with water and sat'd NaCl. After concentration and drying, the (2R,3S)-3-benzyloxycarbonylamino-2-benzoyloxyphenylpropionic acid was obtained as a white foamy solid (0.86 g).

Example-20

A mixture of (2R,3S)-3-benzyloxycarbonylamino-2-benzoyloxyphenylpropionic acid, 2-trimethylsilylethyl ester (1.1 g) (126 mg, 0.3 mmol), 4-pyrrolidinopyridine (22 mg, 0.15 mmol), DCC (68 mg, 0.32 mmol) and 7-TES-baccatin (70 mg, 0.1 mmol) in 0.4 mL of dry toluene was heated at 50° C. for 7 h. The reaction mixture was then cooled and purified on silica gel eluting with hexane and 15% ethyl acetate/hexane to give the (2R,3S)-3-benzylcarbonylamino-2-benzoyloxyphenylpropionic acid, 7-TES-baccatin ester (108 mg).

Example-21

The 7-TES-baccatin ester from Example-20 (50 mg), ammonium formate (0.5 g) and 10% Pd/C (10 mg) were dissolved in methanol (2 mL) and stirred at room temperature for 4–5 h. The catalyst was removed by filtration and the filtrate was concentrated to dryness. The residue was then dissolved in 1 mL of formic acid and stirred at room temperature overnight. The solution was concentrated to dryness and the crude product was purified on silica gel eluting with ethyl acetate to give Taxol (9 mg) identical with natural taxol by HNMR and HPLC.

We claim:

1. A process for the preparation of taxol and derivatives thereof comprising (a) reacting a β-alkoxycarbonylaminophenylpropionic acid of formula

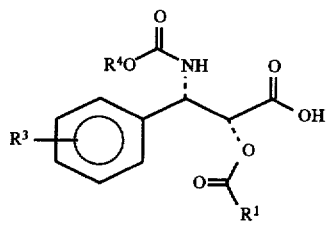

wherein $R^1$ is $C_1$ to $C_{10}$ alkyl, $C_1$ to $C_{10}$ alkoxyl, phenyl or substituted phenyl; $R^3$ is hydrogen, loweralkyl, loweralkoxyl, di-loweralkylamino or halo; and $R^4$ is benzyl, t-butyl, allyl, trichloroethyl, or 9-fluorenylmethyl, with a 13-hydroxy taxane to produce a β-alkoxycarbonylaminophenylpropionic ester of said taxane at C-13; and (b) cleaving the β-alkoxycarbonyl from said β-alkoxycarbonylaminophenylpropionic ester of taxane to produce a β-amido-α-hydroxybenzenepropanoic ester of said taxane.

2. A process according to claim 1 wherein $R^1$ is phenyl, t-butoxyl or 4-chlorophenyl and $R^3$ is hydrogen.

3. A process according to claim 1 comprising (a) reacting a β-alkoxycarbonyl-aminophenylpropionic acid of formula

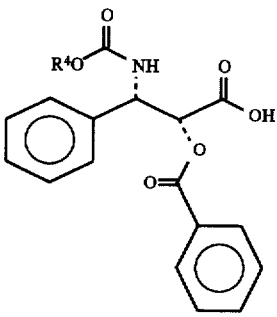

with a taxane of formula

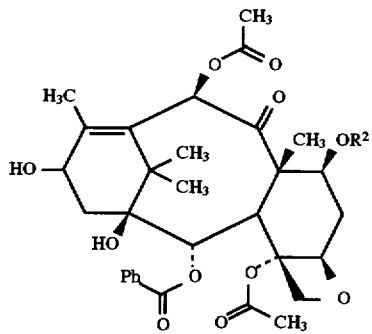

to produce an β-alkoxycarbonylaminophenylpropionic ester at C-13 of taxane of formula

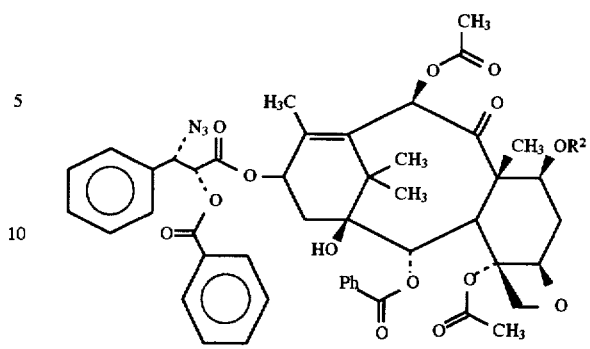

and (b) cleaving the β-alkoxycarbonyl of said β-alkoxycarbonylaminophenylpropionic ester of taxane to produce a β-amido-α-hydroxybenzenepropanoic ester of said taxane of formula

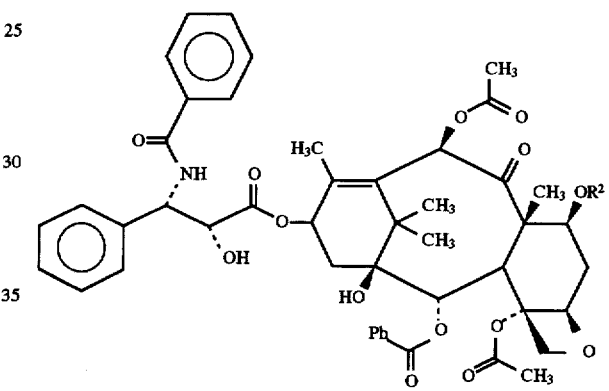

wherein $R^2$ is a protecting group for an alcohol.

4. A process according to claim 3 wherein said protecting group for an alcohol is 1,1,1-trichloroethoxycarbonyl, trialkylsilyl or aryldialkylsilyl.

5. A process according to claim 4 wherein said protecting group for an alcohol is tri-n-hexylsilyl.

6. A process according to claim 3 comprising the additional step of cleaving said protecting group for an alcohol to produce taxol.

7. A process according to claim 3 wherein said step of cleaving the β-alkoxycarbonyl of said β-alkoxycarbonylaminophenylpropionic ester also cleaves said protecting group for said alcohol, whereby a 2',7-dihydroxy-3'-amidoester is produced in a single reaction.

* * * * *